United States Patent [19]
Subramanian et al.

[11] Patent Number: 5,780,253
[45] Date of Patent: Jul. 14, 1998

[54] SCREENING METHOD FOR DETECTION OF HERBICIDES

[75] Inventors: Venkiteswaran Subramanian, Danville; Anne G. Toschi, Burlingame, both of Calif.

[73] Assignee: Sandoz Ltd., Basel, Switzerland

[21] Appl. No.: 752,990

[22] Filed: Nov. 21, 1996

Related U.S. Application Data

[63] Continuation of Ser. No. 434,826, May 4, 1995, abandoned.

[51] Int. Cl.$^6$ .................. C12Q 1/48; C12Q 1/32; C12Q 1/37; C12Q 1/00
[52] U.S. Cl. .................. 435/15; 435/18; 435/26; 435/23; 435/4; 536/23.6; 536/23.2; 536/24.3; 536/26.11; 536/26.12; 536/26.13
[58] Field of Search .................. 435/15, 18, 26, 435/23, 4; 536/23.6, 23.2, 24.3, 26.11, 26.12, 26.13

[56] References Cited

U.S. PATENT DOCUMENTS

| | | | |
|---|---|---|---|
| 4,400,529 | 8/1983 | Chin | 71/103 |
| 4,433,999 | 2/1984 | Hyzak | 71/103 |
| 4,645,527 | 2/1987 | Amoti et al. | 71/103 |
| 4,802,912 | 2/1989 | Baker | 71/103 |

OTHER PUBLICATIONS

Heim et al. Pesticide Biochem & Physiol; vol. 53, pp. 138–145 (1995).
Hatch, MD.; Phytochem, vol. 6., pp. 115 to 119, (1967).
Haworth et al. J. Agric. Food Chem, vol. 38, pp. 1271–1273, 1990.
Nishimura et al; Phytochem; vol. 34, pp. 613–615, (1993).

*Primary Examiner*—Louise N. Leary
*Attorney, Agent, or Firm*—Lynn Marcus-Wyner; Michael P. Morris

[57] ABSTRACT

This invention relates to novel screening methods for identifying compounds that specifically inhibit a biosynthetic pathway in plants. Enzymes which are specifically affected by the novel screening method include plant purine biosynthetic pathway enzymes and particularly the enzymes involved in the conversion of inosine monophosphate to adenosine monophosphate and inosine monophosphate to guanosine monophosphate. Further the invention relates to compositions and method of use comprising herbicidally effective amounts of the identified compounds.

18 Claims, 5 Drawing Sheets

1

SCREENING METHOD FOR DETECTION OF HERBICIDES

This is a CONTINUATION of application Ser. No. 08/434,826, filed on May 4, 1995 now abandoned.

BACKGROUND OF THE INVENTION

In recent years, a number of herbicides have been found to inhibit enzymes in specific biosynthetic pathways, for example glyphosate inhibits enzymes in the aromatic amino acid pathway and imidazolinones and sulfonylureas inhibit enzymes in the branched amino acid pathway. Rapid screening methods have been devised to identify potential herbicidal compounds which target specific enzymes or metabolic pathways. Since typically a test or probe compound is determined to be herbicidal by spraying the compound on a whole plant or plant part or applying the compound to the soil prior to seedling emergence, with chemical effect determined at a specific time interval after chemical application, the screening methods utilizing the inhibition of enzymes in a metabolic pathway provide an efficient and rapid method for assessing the herbicidal properties of probe compounds.

We have discovered that the herbicidal activity of the known compound hydantocidin and at least some of its derivatives is a result of their inhibition of AMP biosynthesis in the plant purine biosynthetic pathway. We have further discovered a rapid means for screening potential herbicidal compounds acting on the enzymes in the plant purine biosynthetic pathway.

SUMMARY OF THE INVENTION

This invention relates to novel screening methods for identifying compounds that specifically inhibit a metabolic target site or pathway in plants. Enzymes which are specifically targeted by the novel screening method include plant purine biosynthetic pathway enzymes and particularly enzymes that inhibit AMP and GMP biosynthesis.

Therefore, one of the main objectives of the invention was to develop a screening assay for identifying inhibitory compounds of the plant purine biosynthetic pathway that could potentially act as herbicides.

Accordingly, the present invention comprises a method of identifying potential inhibitors of the plant purine biosynthetic pathway which are potential herbicides comprising testing a probe compound, in a lethal concentration and reversal assay. This two-step procedure includes determining the lethal concentration of the probe compound and reversion of the inhibition caused by the probe compound at the lethal concentration in the presence of antidote compounds described hereinbelow. The invention further relates specifically to novel compounds which inhibit IMP, AMP and GMP biosynthesis, and specifically the target enzymes adenylosuccinate synthetase (ADSS), adenylosuccinate lyase (ASL), IMP dehydrogenase or GMP synthase.

Another aspect of the present invention is a method for the control of undesirable plant growth which comprises applying to a locus where control is desired a herbicidally effective amount of an inhibitory compound identified according to the method disclosed herein.

According to still another aspect, the invention is a herbicidal composition comprising an inhibitor compound of the invention as an active ingredient in combination with an agriculturally acceptable carrier.

DETAILED DESCRIPTION OF THE INVENTION

Figure 1A:
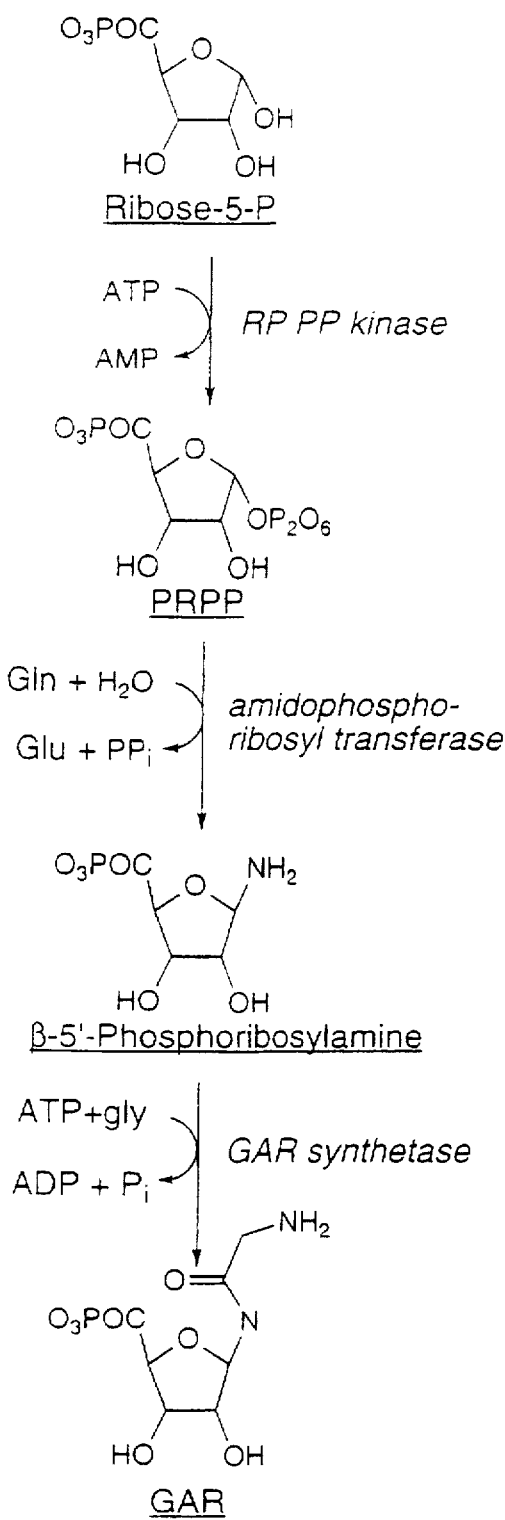
FIG. 1 depicts the IMP biosynthetic pathway.

To assist in interpreting the means and scope of the present invention, the following terms and abbreviations are intended to have the meaning described herein:

ADSS=adenylosuccinate synthetase.
AMP=adenosine monophosphate
ADP=adenosine diphosphate
AICAR=5-aminoimidazole-4-carboxamide ribotide
AICARP=5-aminoimidazole-4-carboxamide ribotide 5' phosphate
AIR=aminoimidazole-4-carboxamide-1-b-D-ribofuranosyl-5-monophosphate
AS=adenylosuccinate
ASL=adenylosuccinate lyase
ATP=adenosine triphosphate
GAR=glycinamide ribotide
GA=glycinamide
GDP=guanosine diphosphate
GMP=guanosine monophosphate
GTP=guanosine triphosphate
IMP=inosine monophosphate
XMP=xanthosine monophosphate
NAP-H=5'-Phospho-N-acetyl-hydantocidin also known as N-acetylphosphohydantocidin
PRPP=phosphoribosyl pyrophosphate
R5P=ribose-5-phosphate The term "IMP biosynthesis" means the conversion of R5P into IMP. "AMP biosynthesis" means the conversion of IMP into AMP. Specifically the term "AMP biosynthetic inhibitory effective amount" means an amount of a probe compound which causes a significant decrease in the ability of ADSS or ASL to convert the substrate, IMP into product, AMP in the presence of GTP and aspartate as measured by quantified enzymatic activity as generally known to those skilled in the art.

"GMP biosynthesis" means the conversion of IMP into GMP. Specifically the term "GMP biosynthetic inhibitory effective amount" means an amount of a probe compound which causes a significant decrease in the ability of IMP dehydrogenase or GMP synthase to convert the substrate, IMP into product, GMP in the presence of ATP and glutamine as measured by quantified enzymatic activity as generally known to those skilled in the art.

A "probe compound" is a compound used in the methods described herein which potentially inhibits either directly or indirectly one or more of the plant purine biosynthetic pathway enzymes. Unless indicated otherwise, the term "plant purine biosynthetic pathway enzyme" as used herein refers to any enzyme which is involved in the purine biosynthetic pathway as depicted in FIGS. 1 and 2 and includes PRPP kinase, amidophosphoribosyl transferase, GAR synthetase, GAR transformylase, FGAM synthetase, AIR synthetase, AIR carboxylase, SACAIR synthetase, adenylosuccinate lyase, AICAR transformylase, IMP cyclohydrolase, IMP dehydrogenase, GMP synthase, adenylosuccinate synthase and adenylosuccinate lyase. A plant purine biosynthetic pathway inhibitor is an inhibitor or probe compound that inhibits any of plant purine biosynthetic pathway enzymes.

Lethal concentration is the concentration of a probe compound which causes about 80% or greater growth inhibition when compared to a control, and more preferably causes about 90% or greater growth inhibition. LC 90 (also referred to as LD 90 by those skilled in the art) is the concentration used to cause 90% growth inhibition of the plants as compared to control plants. No growth would be equal to 100% growth inhibition.

The term "plant material" includes seed; seedlings; parts of young plants, such as meristematic tissue, leaf tissue, root tissue, and shoot tissue; callus and other cultures. Preferred plant materials of the screening method of the present invention are seeds, particularly Arabidopsis seed and grass seed such as bent grass.

The terms "herbicide" and "herbicidal" used herein denote the inhibitive control or modification of undesired plant growth. Inhibitive control or modification includes all deviation from natural development such as for example, total killing, growth retardation, defoliation, desiccation, stunting, tillering, stimulation, leaf burn and dwarfing. The term "herbicidally effective amount" denotes any amount which achieves such control or modification when applied to undesired plants themselves or to a locus where control is desired. The term "plant" is intended to include germinant seed, emerging seedlings and established vegetation including roots and above ground portions.

Test conditions suitable for growth are those conditions wherein the control plant material used in the screen, described herein, will grow normally. These conditions are easily determined by one skilled in the art. Reversal conditions are those conditions in which inhibition which occurs at the lethal concentration of a probe compound is reversed as determined by exposure of the plant material to combinations of the probe compound and to one or more antidote compounds. The recovery of growth is about at least 50% or more. An antidote compound is a compound that causes reversal of inhibition of a probe compound. As an example, with respect to inhibitors of ADSS, antidotes would include AMP, ADP, adenosine and adenine. The antidotes for inhibitors of ASL would also include adenine, AMP, adenosine and ADP; the antidotes for inhibiting GMP synthase would include GMP, guanine and guanosine and the antidote compounds for IMP dehydrogenase would include XMP, GMP, guanine and guanosine.

Compounds which are particularly preferred are those compounds which inhibit GMP biosynthesis and AMP biosynthesis. Particularly preferred target enzymes are ADSS, ASL, IMP dehydrogenase and GMP synthase. The screening method described herein provides an efficient and rapid way for determining the herbicidal potential of probe compounds. Compounds identified by the method described herein may be used as herbicides to inhibit plant growth.

To identify inhibitory compounds, a lethal concentration and reversal assay screen was developed which utilizes Arabidopsis seeds. This assay involves a two-step screening. In the first step, a lethal concentration of a probe compound is determined and reversal of inhibition is determined in the second step. For the herbicide, hydantocidin, inhibition at the lethal concentration in the presence of AMP, ADP or adenine is demonstrated to be completely reversed. The % recovery of growth is then determined and is about between 50 and 100%.

The Arabidopsis bioassay results reported in Table 1 indicate that hydantocidin, N-acetyl hydantocidin (NAP-H) and hadacidin are blocking AMP biosynthesis.

In one embodiment, the invention is a method for identifying a probe compound that inhibits plant AMP biosynthesis, said method comprising:

a) exposing plant material capable of expressing the enzymes adenylosuccinate synthetase and adenylosuccinate lyase to a concentration range of a probe compound;

b) determining a lethal concentration range of said probe compound;

c) exposing plant material capable of expressing said enzyme to the lethal concentration range of said probe compound and concurrently exposing said material to a concentration range of one or more antidote compounds; and d) identifying a probe compound that inhibits growth of the plant material at a lethal concentration but does not inhibit growth of the plant material when exposed in combination to the antidote compound.

A further embodiment includes a method for identifying a probe compound that inhibits plant AMP biosynthesis, said method comprising a two-step procedure.

a) wherein the first step includes the determination of a lethal concentration which comprises:
1) maintaining plant material capable of expressing the enzymes adenylosuccinate synthetase and adenylosuccinate lyase under test conditions suitable for growth of the plant material;
2) contacting a probe compound at a concentration range of about 0.01 ppm to about 500 ppm with the plant material of 1);
3) allowing the probe compound and plant material to incubate; and
4) measuring the inhibition of growth of the plant material and determining the lethal concentration of the probe compound; and b) wherein the second step includes the determination of reversal conditions which comprises:
5) maintaining plant material as stated in step 1);
6) contacting the plant material with the probe compound and one or more antidote compounds wherein the concentration of the probe compound is at about the lethal concentration and the concentration of the antidote compound is in the range of about 0.001 mM to about 5.0 mM;
7) allowing the plant material to grow in the presence of the probe compound and antidote compound;
8) measuring the growth of the plant material and
selecting the probe compound that inhibits growth of the plant material under step a) but does not inhibit growth of the plant material under reversal conditions of step b).

In general, the preferred plant material in the assay is seed material and particularly Arabidopsis seed. However, one skilled in the art could easily use seeds of other plant species or cultures of plant cells. If seed material is used, it is preferable to determine the lethal concentration and the reversal conditions independently after about 5 days, but before 14 days. One skilled in the art would be able to determine the preferred effective concentration range of a probe compound to determine lethal concentration of that particular probe compound by routine experimentation. For example, probe compounds tested in the method should be supplied at a concentration range as described above, about 0.01 ppm to about 500 ppm, a preferred range is about 0.05 ppm to about 250 ppm and more preferred concentration range is about 0.1 to about 100 ppm. Concentrations higher than 500 ppm would be similarly effective but may be wasteful and are usually not necessary. A preferred concentration range of the antidote compound is about 0.001 mM to about 5.0 mM, and more preferably about 0.005 mM to about 1.0 mM.

While it is preferred to determine the lethal concentration at a LC 90 value, values less than 90% can be used, for example 80%. As can be appreciated, the antidote compound will vary depending on the target enzyme. With ADSS, the preferred antidote compounds include ADP, AMP, adenine and adenosine.

Further, the method described herein can be used to discover inhibitors that block any of the fifteen enzymes in the purine biosynthetic pathway depicted in FIGS. 1 and 2. These enzymes are collectively referred to as plant purine biosynthetic pathway enzymes. The method for screening and identifying a compound that inhibits plant purine biosynthetic pathway enzymes comprises a two step procedure, a) the first step includes the determination of a lethal concentration which comprises:
1) maintaining plant material capable of expressing a plant purine biosynthetic pathway enzyme under test conditions suitable for growth of the plant material;
2) contacting a probe compound at a concentration range of about 0.01 ppm to 500 ppm with the plant material of 1);
3) allowing the probe compound and plant material to incubate; and
4) measuring the inhibition of growth of the plant material and determining the lethal concentration of the probe compound;

b) the second step includes the determination of reversal conditions which comprises:
5) maintaining plant material as stated in step 1);
6) contacting the plant material with the probe compound and one or more antidote compounds wherein the concentration of the probe compound is at about the lethal concentration and the concentration of the antidote compounds are in the range of about 0.001 mM to about 5.0 mM;
7) allowing the plant material to grow in the presence of the probe compound and antidote compound;
8) measuring the growth of plant material and identifying a compound that inhibits growth of the plant material under test conditions but does not inhibit growth of the plant material under reversal conditions.

In another preferred embodiment the invention includes a method for identifying a probe compound that inhibits plant AMP biosynthesis, said method comprising a two step procedure, a) wherein the first step includes the determination of a lethal concentration which comprises:
1) adding a concentration range of about 0.01 to about 500 ppm of a probe compound to wells of a support;
2) dispensing media capable of sustaining growth of plant seeds in said wells;
3) adding plant seeds capable of expressing the enzyme adenylosuccinate synthetase or adenylosuccinate lyase to the media in said wells;
4) allowing the probe compound and the seeds to incubate under test conditions suitable for growth of said seed;
5) measuring the inhibition of growth of the seeds; and
6) determining the lethal concentration of the probe compound; and b) wherein the second step includes the determination of reversal conditions which comprises:

7) adding about the lethal concentration of the probe compound to wells in a support;
8) adding one or more antidote compounds separately to said wells;
9) dispensing media capable of sustaining growth in said wells;
10) adding plant seeds capable of expressing the enzymes adenylosuccinate synthetase or adenylosuccinate lyase to said media to said wells;
11) allowing the seeds to germinate in the presence of the probe compound and antidote compound;
12) measuring the growth of said seeds as compared to a control wherein the control lacks the antidote compounds of step 8); and identifying a compound that inhibits growth of the seeds under the lethal concentration but does not inhibit growth of said seeds under reversal conditions.

In another preferred embodiment, the invention includes the above described two-step method for identifying a probe compound that inhibits plant GMP biosynthesis however, the enzymes that are inhibited would include IMP dehydrogenase or GMP synthase. Additionally, the claimed two-step method can be used to identify a probe compound that inhibits IMP biosynthesis.

The media used for seedling growth may be any media suitable for maintaining plant growth and preferably contains macro and micronutrients which are supplemented with a sugar source, preferably sucrose. In a preferred embodiment, the media will be a mixture of the above components and agar which is then dispensed into wells. There are numerous commercially available sources of agar and some examples include Sigma Bacteriological Agar and Phytagar. However, one skilled in the art will appreciate that any type of gelatin material could be suitable.

While the term "well or wells" is used to indicate the space in which the media and plant material are placed, synonymous terms are equally applicable, and include for example, openings, pores, slots, spaces and the like. A support can be any container or material that will hold the media and plant material to provide an environment for plant growth, while tissue culture cell wells are preferred other examples include, pill bottles, petri plates and the like.

Plant growth can be measured by means known to those skilled in the art and include measurements of root growth, leaf growth, inhibition and leaf malformation. In the preferred embodiment seedling growth is measure by scoring shoot, leaf and root growth relative to a control.

One skilled in the art will appreciate that the assay system described herein may be modified in various aspects without changing the essence of the invention. Additionally, one skilled in the art can readily substitute functionally equivalent test methods.

The probe compounds that have been identified according to the invention as inhibiting the plant purine biosynthetic pathway as well as other hydantocidin compounds can be further evaluated by testing the compound on whole plants in typical herbicidal greenhouse tests well known to those skilled in the art.

The purine biosynthetic inhibitors, particularly the AMP biosynthesis inhibitors and GMP biosynthesis inhibitors of the invention may be employed in herbicidal compositions, and these compositions form an important embodiment of the present invention. The purine biosynthetic inhibitor comprises the active ingredient of the composition generally with an inert ingredient. The compositions may be formulated as either concentrated formulations or as dust or granular formulations. The formulations are prepared according to procedures which are conventional in the agricultural arts. In general, the formulations may include 0.01 to 99% by weight of active ingredient, 0 to 40% by weight of agriculturally acceptable surfactant and from 0.1 to 99.99% of solid or liquid diluent(s). The active ingredient consists of at least one compound of the invention or mixtures thereof with other active ingredients. Surfactants are agriculturally acceptable materials which impart emulsifying, spreading, wetting, dispersibility or other surface-modifying properties to formulations. A diluent is any liquid or solid agriculturally acceptable material which may be added to the active constituent to bring it in an easier or improved form.

Further the inhibitory compounds of the present invention may be used to control undesired plant growth and may be used for the control of both broad leaf and grassy weeds in preplant incorporation and pre- and post-emergent application. Inhibitory compounds may also exhibit selectivity in various crops and thus be suited for use in weed control in crops such as but not limited to corn, cotton, wheat, soybean, rice, sugarbeet and sunflower.

The following non-limiting examples are provided to illustrate the invention further.

EXAMPLE 1

Determination of the Lethal Concentration of the Test (Probe) Compounds

Figure 3:
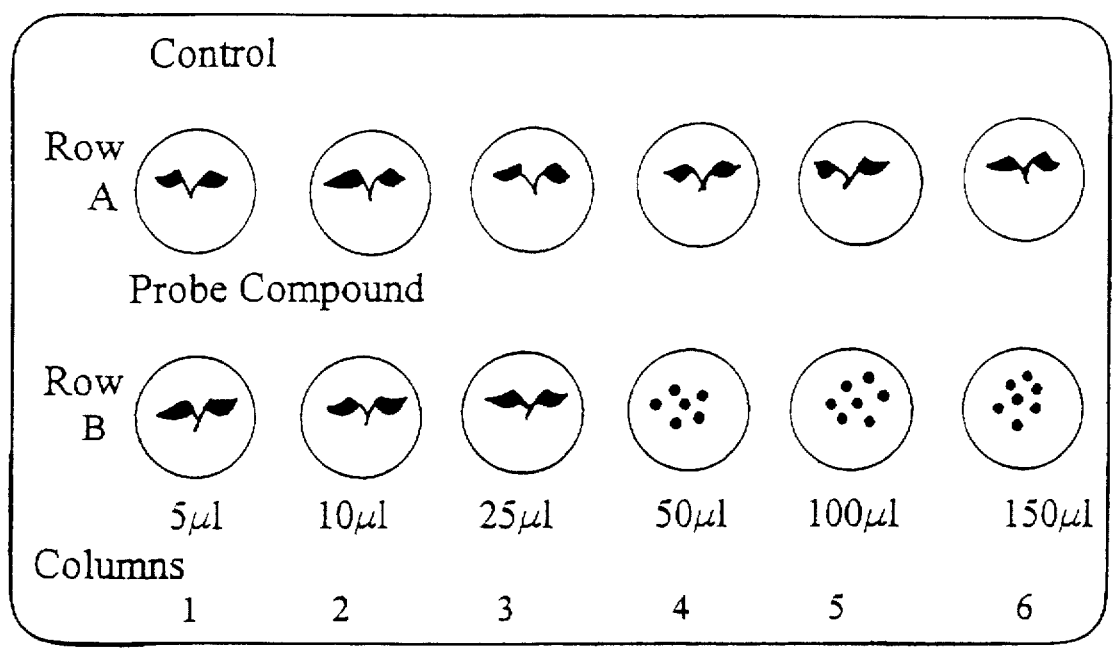
FIG. 3 illustrates schematically the lethal concentration step of the claimed assay procedure. Row A is the control and does not contain a probe compound. Row B contains 6 concentrations or doses of an aqueous solution of the probe compound (5, 10, 25, 50, 100 and 150 µl). In this figure the lethal concentration is 50 µl.

Stock solutions of probe compounds are made at 500 ppm in distilled water or a suitable solvent that does not affect plant growth. Arabidopsis bioassays are conducted in 24-well sterile microtiter plates. In a typical microtiter plate, there are 4 rows of 6 wells each. For simplicity, FIG. 3 shows a control and at least one probe compound. Row A is designated for the control and consists of 6 wells without the addition of a test compound. Row B is designated for a probe compound. Probe compounds are added into the wells in appropriate volumes in µL. Each row of six wells represents a concentration range of 0.1 to 150 ppm. In practice each plate may comprise more rows for additional probe compounds, and as determined from above 4 row plates are typically used.

Each microtiter plate requires 40 ml of Arabidopsis seed media. The seed media consists of 5 ml MS micronutrient 100×concentrated solution and 50 ml MS macronutrient 10×concentrated solution supplemented with 1% w/v of sucrose and brought to 1.0 liter with water. The media is adjusted to pH 6.6. Phytagar is added to the media for a final concentration of 0.7% w/v. The media is autoclaved under standard conditions for 20 minutes. After cooling the media to about 45° C., 1.0 ml of the media is dispensed in each well of the microtiter plate.

About 100 mg of Arabidopsis seeds are sterilized by rinsing thoroughly in 50 ml of 20% bleach containing 2.0 µL/ml of 20% Triton X100. Typically this is done with 45 ml of sterilant in a 50 ml sterile tube. After shaking the seeds for 10 minutes, the seeds are allowed to settle under gravity, the sterilant is removed and the seeds are rinsed six times with sterile water. After the final rinse, all but approximately 3.0 ml of the water is removed. The sterile seeds can be stored at 4° C. for approximately 3 weeks and used repeatedly. Between 10–20 seeds are dispensed in each well using a 1.0 ml pipette. The microtiter plate is then closed, taped and incubated at about 28° C. for 7 days. Growth is scored visually, as a % of control. 100% growth inhibition is equivalent to no growth, for example seeds only; 95% growth inhibition is equivalent to 5% growth, for example only root growth and small leaf growth; and 90% growth inhibition is equivalent to 10% growth, for example about 1/10 of the control growth. Concentration of the compound causing 90% or greater growth inhibition (LC 90) compared to controls is designated as lethal concentration. Results of a typical assay are shown in FIG. 3. Using this procedure, lethal concentrations of hydantocidin, N-acetyl hydantocidin, N-acetylphosphohydantocidin and hadacidin were determined as approximately 2.0, 12.0, 8.0 and 50 µM respectively. The calculation for lethal dose is as follows:

a. $\dfrac{(\mu l \text{ of lowest dose showing } 90\% \text{ growth inhibition})(\text{ppm tested})}{1000} = \text{ppm in well}$ b. $\dfrac{(\text{ppm in well})(1000)}{\text{mw of the compound}} = \mu M \text{ of compound in the well}$

EXAMPLE 2

Identification of AMP Biosynthesis Inhibitors

Figure 4:
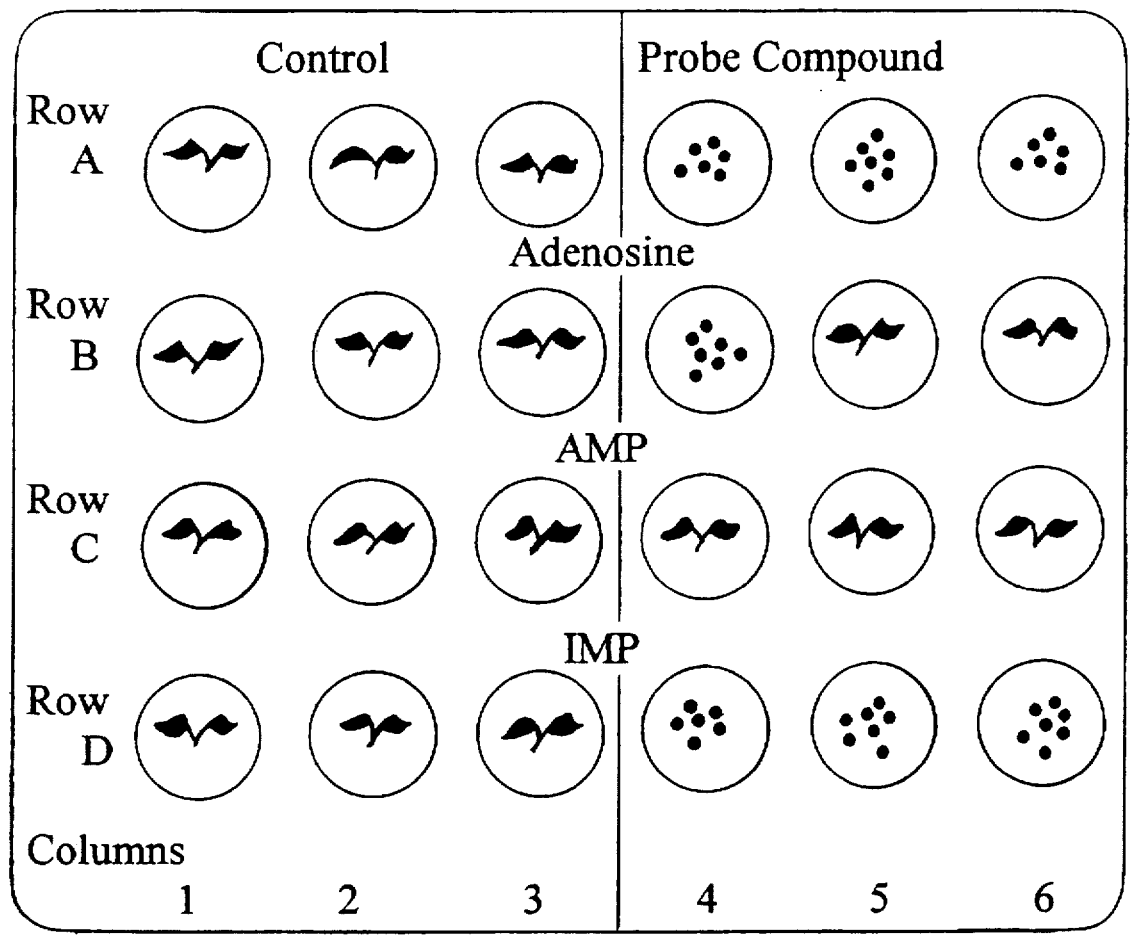
FIG. 4 illustrates schematically the reversal step of the claimed assay procedure.

Stock solutions (0.5% w/v) of antidote compounds; ADP, IMP and adenine are prepared at 2% w/v (except where indicated). The solutions are filter sterilized prior to addition. FIG. 4 represents a typical set up in a reversion assay for discovering inhibitors of AMP biosynthesis.

The left side (columns 1–3) of the 24-well microtiter plate is designed for controls, and the right side (columns 4–6) are designated for one probe compound. The first row (A) does not have added antidote and is used as a check. Rows B, C and D are supplemented with three doses of an antidote for the control and probe compound. In the example shown in FIG. 4, the antidotes used are adenosine, AMP and IMP. The three doses are 50, 100 and 150 µl respectively of the stock solutions.

Forty ml of Arabidopsis growth media as described in Example 1 is sterilized and allowed to cool to about 45° C. A probe compound (at 1.5×lethal concentration) is added to columns 4 through 6 (right half of the plate). Media is distributed at 1.0 ml per well to all wells. Sterile seeds are added to each well as described above. As in Example 1, the plate is incubated and growth is scored.

Using this procedure for hydantocidin, it is determined that growth occurred in all wells in columns 1 through 3. This result indicates that the selected antidote compounds, IMP, adenosine and AMP have no effect on the growth of the plant. Growth is not observed in the top row, wells 4 through 6 due to the lethal effects of the probe compound. Also IMP did not reverse growth inhibition and therefore is not an antidote for this particular test. Complete growth is observed in rows B and C, wells 4 through 6, indicating that adenosine and AMP are able to reverse the growth inhibition. Lack of growth in well C4 (row C, column 4) may be due to insufficient adenosine to reverse growth inhibition.

The above two-step process is conducted with hydantocidin, (Hyd); N-acetyl hydantocidin, (NA-H); NAP-H and hadacidin, (Had), in the presence of various antidotes and the results are shown in Table 1 below. All four compounds specifically block the conversion of IMP to AMP.

TABLE 1

Effect of Various Antidotes on Arabidopsis Inhibition by Compounds Listed

| Antidote Added to Standard Arabidopsis Growth Media | Concentration (mM) | Growth, % of Control | | | |
|---|---|---|---|---|---|
| | | Hvd | NA-H | NAP-H | Had |
| No antidote | 0 | 0 | 0 | 0 | 0 |
| Adenine | 0.5–5.0 | 60 | 60 | 65 | 55 |
| Adenosine | " | 80–100 | 80–100 | 80–100 | 80–100 |
| Guanine | " | 0 | 0 | 0 | 0 |
| Guanosine | " | 0 | 0 | 0 | 0 |
| Adenosine + Guanosine | " | 80 | 80 | 80 | 80 |
| Cytidine + Uridine | " | 0 | 0 | 0 | 0 |
| AMP | " | 100 | 100 | 100 | 100 |
| ADP | " | 100 | 100 | 100 | 100 |
| ATP | " | 40 | 40 | 40 | 40 |
| IMP | " | 5 | 5 | 5 | 5 |
| Hypoxanthine | " | 0 | 0 | 0 | 0 |

Growth is not observed in the presence of Hyd, NA-H, NAP-H or Had without the antidote, and 0 is equal to no growth.

EXAMPLE 3

Identification of GMP Biosynthesis Inhibitors

The above described two-step process in Examples 1 and 2 is conducted in the same manner with Mycophenolic Acid (MPA) in the presence of various antidotes and the results are shown in Table 2 below. MPA is a known inhibitor of IMP to GMP conversion. The lethal concentration is determined to be 12.5 ppm.

TABLE 2

Effect of Various Antidote Compounds on Arabidopsis Inhibition by MPA

| Antidote Added to Standard Arabidopsis Growth Media | Concentration (mM) | Growth, % of Control |
|---|---|---|
| No Antidote | 0 | 0 |
| Adenine | 0.5–5.0 | 0 |
| Adenosine | " | 5 |
| Guanine | " | 40 |
| Guanosine | " | 80 |
| AMP | " | 5 |
| GMP | " | 90 |
| IMP | " | 5 |

Growth is not observed in the presence of MPA without the antidote, and (0 is equal to no growth.

EXAMPLE 4

Identification of IMP Biosynthesis Inhibitors

The above descibed two-step process in Examples 1 and 2 is conducted in the same mannner with 1,2,4-triazole-3-carboxamide-1-ribose (TCR) in the presence of various antidotes and the results are shown below in Table 3. The lethal concentration of TCR is determined to be 200 ppm.

TABLE 3

Effect of Various Antidote Compounds on Arabidopsis Inhibition by TCR

| Antidote Added to Standard Arabidopsis Growth Media | Concentration (mM) | Growth, % of Control |
|---|---|---|
| No Antidote | 0 | 0 |
| AMP | 0.5–5.0 | 70 |
| IMP | " | 70 |
| GMP | " | 80 |

Growth is not observed in the presnece of TCR without the antidote, and (0) is equal to no growth.

EXAMPLE 5

Herbicidal Greenhouse Tests

The above described Arabidopsis screening method demonstrates good correlation with herbicidal greenhouse data. In general, the herbicidal greenhouse tests are conducted as follows: A probe compound is weighed and dissolved in a stock solution consisting of acetone or DSMO:deionized water (1:1) and 0.5% adjuvant mixture. Dilutions from this stock solution are performed to allow for preparation of spray solutions consisting of single doses applied at a level equivalent to either 4.0, 1.0 or 0.25 kg/ha of active ingredient. The solutions are applied by a linear track sprayer set to deliver 1000 L/ha spray volume. Both broadleaf and grassy weed species are tested. Herbicidal control is evaluated as % injury with 100% injury considered complete control. The herbicidal effect is determined in both pre-emergence and post-emergent studies.

In post-emergent studies each dose of compound is applied to the foliage of the selected weed species. The weed plants are allowed to grow in the greenhouse and visually evaluated at 1, 7 and 19 days after treatment.

When a probe compound is screened in the Arabidopsis bioassay herein described and is found to be inactive, the same compound is also found to be inactive in the herbicidal screening studies at 1.0 kg/ha. Inactivity is considered to be on average approximately 10% or less injury. Likewise, a probe compound which is determined to be active in the Arabidopsis assay and wherein reversion of growth inhibition is determined with AMP, the compound is found to cause weed injury in the herbicidal screening tests. The amount of injury varies with each probe compound and with the type of weed species, but in general overall injury when the compound is applied at 1.0 kg/ha is greater than 40% and in some weed species the injury will be greater than 70%.

One skilled in the art is aware of procedures to make various hydantocidin derivatives. These methods are disclose in references such as, DE 4129728, DE 4129616, JP 2167283 and in U.S. patent application Ser. No. 315,796 filed Sep. 30, 1994. These references are hereby incorporated by reference.

What is claimed is:

1. A method for identifying a probe compound that inhibits plant AMP biosynthesis, said method comprising a two-step procedure,
   a) the first step includes the determination of a lethal concentration which comprises:
      1) maintaining plant material capable of expressing the enzyme adenylosuccinate synthetase and adenylosuccinate lyase under test conditions suitable for the growth of the plant material;

2) contacting a probe compound at a concentration range of about 0.01 ppm to about 500 ppm with the plant material of 1);

3) allowing the probe compound and plant material to incubate; and 4) measuring the inhibition of growth of the plant material and determining the lethal concentration of the probe compound;

b) the second step includes the determination of reversal conditions which comprises:

5) maintaining the plant material as stated in step 1);

6) contacting the plant material with the probe compound and one or more antidotes compounds wherein the concentration of the probe compound is at the lethal concentration and the concentration of the antidote compound is in the range of 0.001 to about 5.0 mM;

7) allowing the plant material to grow in the presence of the probe compound and antidote compound;

8) measuring the growth of the plant material and selecting the probe compound that inhibits growth of the plant material under step a) but does not inhibit growth of the plant material under reversal conditions of step b) and wherein the plant material is seed material.

2. A method according to claim 1 wherein the plant material is Arabidopsis seed.

3. A probe compound which inhibits AMP biosynthesis identified according to the method of claim 1.

4. The method according to claim 2 wherein the seeds are Arabidopsis seeds and the first step includes:

1) adding a concentration range of about 0.01 to 500 ppm of a probe compound to wells of a support;

2) dispensing media capable of sustaining seed growth in said wells;

3) adding Arabidopsis seeds capable of expressing the enzyme adenylosuccinate synthetase and adenylosuccinate lyase to said wells;

4) allowing the probe compound and the seeds to incubate under test conditions suitable for growth of said seeds;

5) measuring the inhibition of seed growth; and 6) determining the lethal concentration of the probe compound;

and wherein the second step includes:

7) adding about the lethal concentration of the probe to wells in a support;

8) adding one or more antidote compounds separately to said wells;

9) dispensing media capable of sustaining plant growth in said wells;

10) adding Arabidopsis seeds capable of expressing the enzymes adenylosuccinate synthetase and adenylosuccinate lyase to said wells;

11) allowing the seeds to germinate in the presence of the probe compound and antidote compound;

12) measuring the growth of said seeds as compared to control seeds wherein the control seeds are grown in wells lacking the antidote compound of step 8) and identifying a compound that inhibits growth of the Arabidopsis seeds under the lethal concentration but does not inhibit the growth of said seeds under reversal conditions.

5. A probe compound which inhibits AMP biosynthesis identified according to the method of claim 4.

6. A herbicidal composition comprising as an active ingredient a herbicidally effective amount of a probe compound that inhibits AMP biosynthesis selected according to the method of claim 4.

7. A method of controlling undesired plant growth by applying to a locus where control is desired a herbicidal composition according to claim 6.

8. A method for screening and selecting a probe compound that inhibits an enzyme in the plant purine ribonucleotide biosynthetic pathway selected from the group consisting of PRPP kinase, amidophosphoribosyl transferase, GAR synthetase, GAR transformylase, FGAM synthetase, AIR synthetase, AIR carboxylase, SACAIR synthetase, adenylosuccinate lyase, AICAR transformylase, IMP cyclohydrolase, IMP dehydrogenase, GMP synthase, adenylosuccinate synthase and adenylosuccinate lyase, said method comprising a two-step procedure:

a) wherein the first step includes the determination of a lethal concentration which comprises:

1) maintaining plant material capable of expressing said enzyme under test conditions suitable for the growth of the plant material;

2) contacting a probe compound at a concentration range of about 0.01 ppm to about 500 ppm with the plant material of 1);

3) allowing the probe compound and plant material to incubate; and 4) measuring the inhibition of growth of the plant material and determining the lethal concentration of the probe compound;

b) wherein the second step includes the determination of reversal conditions which comprise 5) maintaining the plant material as stated in step 1);

6) contacting the plant material with the probe compound and one or more antidotes compounds wherein the concentration of the probe compound is at the lethal concentration and the concentration of the antidote compound is in the range of 0.001 to about 5.0 mM;

7) allowing the plant material to grow in the presence of the probe compound and antidote compound;

8) measuring the growth of the plant material and selecting the probe compound that inhibits growth of the plant material under test conditions of step a) but does not inhibit growth of the plant material under reversal conditions of step b) wherein the plant material is Arabidopsis seed.

9. The method according to claim 8 wherein the enzyme that is inhibited is selected from the group consisting of IMP dehydrogenase and GMP synthase.

10. The method according to claim 8 wherein an IMP biosynthetic enzyme is inhibited.

11. The probe compound which inhibits an enzyme in the plant purine ribonucleotide biosynthetic pathway selected according to the method of claim 8.

12. A herbicidal composition comprising as an active ingredient a herbicidally effective amount of a probe compound that inhibits an enzyme as defined in claim 8 and selected according to the method of claim 8.

13. A method of controlling undesired plant growth by applying to a locus where control is desired a herbicidal composition according to claim 12.

14. A herbicidal composition comprising as an active ingredient an herbicidally effective amount of a probe compound that inhibits AMP biosynthesis identified according to the method of claim 1.

15. A method according to claim 1 wherein the seed is Arabidopsis seed and the antidote compound is selected from the group consisting of ADP, AMP, adenosine or adenine.

16. The method according to claim 1 wherein the enzyme that is inhibited is adenylosuccinate synthetase.

17. A probe compound identified according to the method of claim 16 which inhibits the enzyme adenylosuccinate synthetase.

18. A herbicidal composition comprising as an active ingredient an herbicidally effective amount of the compound according to claim 17.

* * * * *

UNITED STATES PATENT AND TRADEMARK OFFICE
CERTIFICATE OF CORRECTION

PATENT NO. : 5,780,253
DATED : July 14, 1998
INVENTOR(S) : SUBRAMANIAN, ET AL.

Page 1 of 2

Figure 1B:
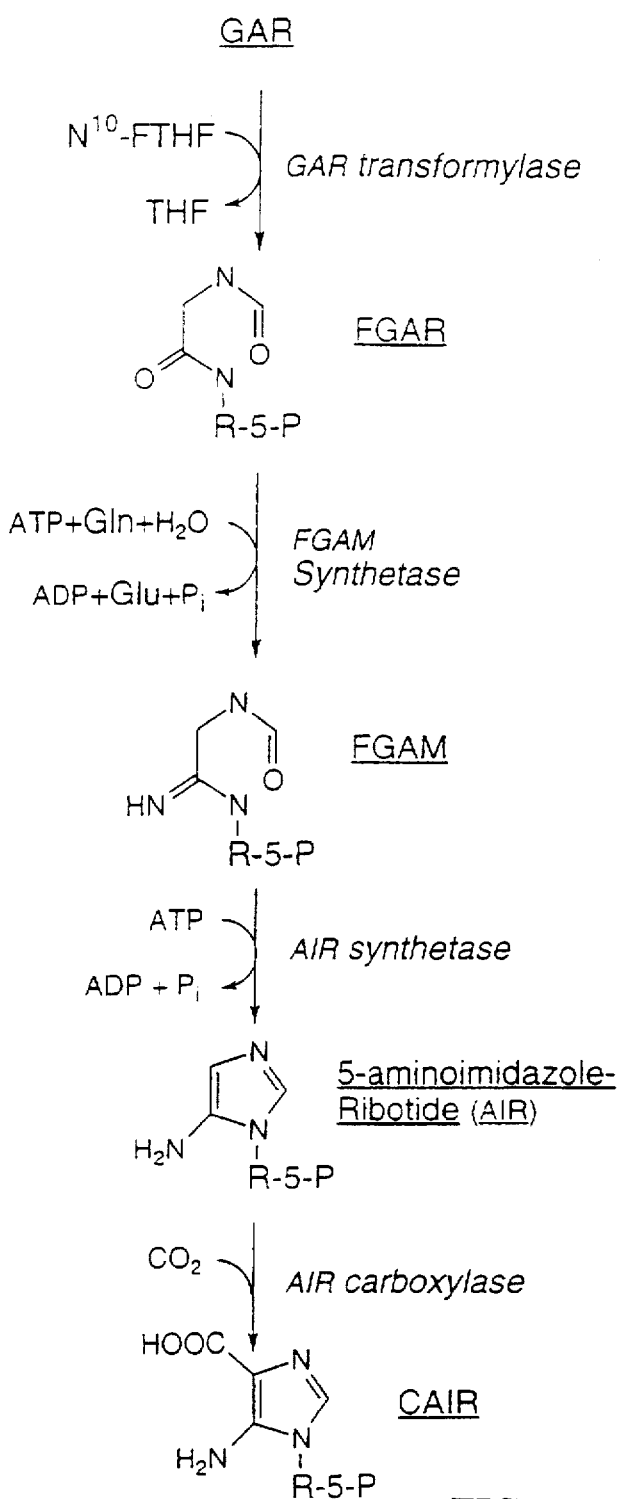
Figure 1C:
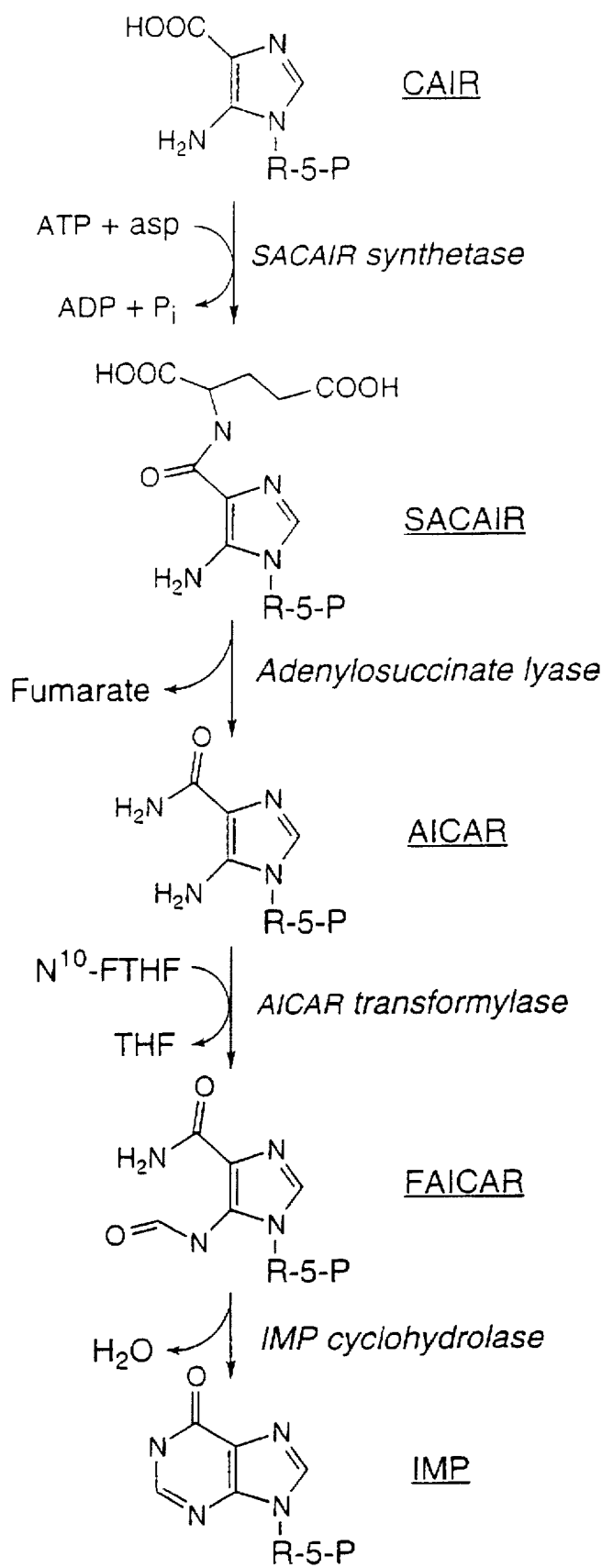
Figure 2:
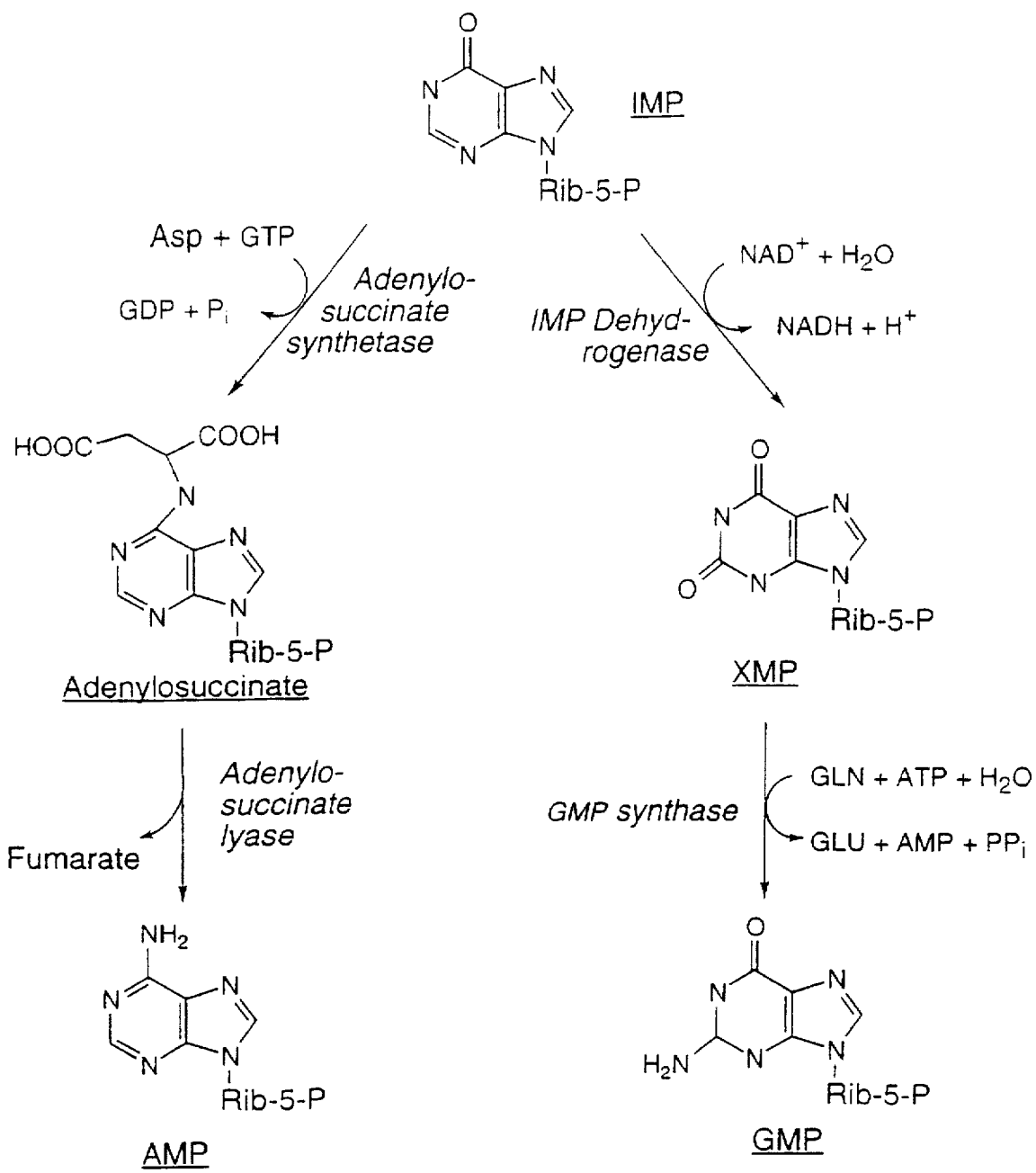
FIG. 2 depicts the pathway for the conversion of IMP to AMP and GMP.

It is certified that error appears in the above-identified patent and that said Letters Patent is hereby corrected as shown below:

Col. 1 and 2, under "Brief Description of the Figures",

For Figure 1 - delete,

"Figure 1 depicts the IMP biosynthetic pathway," please insert,

--- Figures 1A, 1B and 1C depict the IMP biosynthetic pathway. Figure 1A illustrates the pathway from ribose-5-P to CAR; Figure 1B illustrates the pathway from CAR to CAIR; and Figure 1C illustrates the pathway from CAIR to IMP. --- ;

for Figure 3, line 5-after the sentence,

"Row B contains 6 concentrations or doses of an aqueous solution of the probe compound." Please insert, --- In this example the lethal concentration is at 50 µl. Using an initial concentration of 500 ppm and a molecular weight of 400, the dose is 25 ppm and the final concentration is 62.5 µM. --- ;

for Figure 4 - after the phrase,

"... claimed assay procedure." please insert,

--- Columns 1 through 3 are controls (no probe compound). Columns 4 through 6 contain the test compound at twice lethal concentration (determined from lethal concentration assay). Antidotes are added in rows B - C. Row B is supplemented with the antidote adenosine. Row C is supplemented with the antidote AMP, and row D is supplemented with the antidote IMP. Three doses of antidotes are used. Columns 1 and 4 contain 50 µl antidote. Columns 2 and 5 contain 100 µl antidote. Columns 3 and 6 contain 150 µl antidote. --- ;

UNITED STATES PATENT AND TRADEMARK OFFICE
CERTIFICATE OF CORRECTION

PATENT NO. : 5,780,253
DATED : July 14, 1998
INVENTOR(S) : Subramanian, et al.

Page 2 of 2

It is certified that error appears in the above-identified patent and that said Letters Patent is hereby corrected as shown below:

Col. 2, line 62,
  delete "Figures 1 and 2" and insert --- Figures 1A, 1B, 1C and 2 ---.
Col. 1, line 5, delete "Figures 1 and 2', and insert --- Figures 1A, 1B, 1C and 2 ---.

Signed and Sealed this

Twenty-ninth Day of June, 1999

Attest:

Q. TODD DICKINSON

*Attesting Officer*

*Acting Commissioner of Patents and Trademarks*